(12) United States Patent
Sridharan et al.

(10) Patent No.: US 10,438,697 B2
(45) Date of Patent: Oct. 8, 2019

(54) PASSIVE WIRELESS FOOTPEDAL FOR MEDICAL APPLICATIONS

(71) Applicant: General Electric Company, Schenectady, NY (US)

(72) Inventors: Pradeep Kumar Sridharan, Bangalore (IN); Muthu Revathy Authuvan, Tamil Nadu (IN); Narasimha Murthy Vinay, Bangalore (IN); Hiteshkumar Thakarshibhai Boda, Bangalore (IN); Carlos Martinez Ferreira, Paris (FR); Shijin Krishna, Bangalore (IN)

(73) Assignee: General Electric Company, Schenectady, NY (US)

( * ) Notice: Subject to any disclaimer, the term of this patent is extended or adjusted under 35 U.S.C. 154(b) by 319 days.

(21) Appl. No.: 15/333,739

(22) Filed: Oct. 25, 2016

(65) Prior Publication Data

US 2018/0113983 A1    Apr. 26, 2018

(51) Int. Cl.
*G06F 19/00*       (2018.01)
*G16H 40/63*       (2018.01)
(Continued)

(52) U.S. Cl.
CPC ............ *G16H 40/63* (2018.01); *A61B 17/00* (2013.01); *A61B 90/98* (2016.02); *G05B 19/414* (2013.01);
(Continued)

(58) Field of Classification Search
CPC ................. G16H 40/63; G05B 19/414; G05B 2219/23056
See application file for complete search history.

(56) References Cited

U.S. PATENT DOCUMENTS 4,313,258 A * 2/1982 Kindig ............... H01R 43/04
29/596
7,463,313 B2  12/2008 Zwart
(Continued)

FOREIGN PATENT DOCUMENTS

CN    107970073 A *  5/2018  ............. A61B 90/98
EP    2 178 023 A2    4/2010
(Continued)

OTHER PUBLICATIONS

Extended European Search Report and Opinion issued in connection with corresponding EP Application No. 16204700.5 dated Aug. 8, 2017.

*Primary Examiner* — Laura M Menz
(74) *Attorney, Agent, or Firm* — Boyle Fredrickson, S.C.

(57) ABSTRACT

In the present invention, a control device for use in connection with a medical device or system in order to operate various functions of the medical device or system is provided that does not require a wired connection or internal power source for the operation of the control device. The control device in certain embodiments can take the form of a footpedal that is formed without electronics, without a printed circuit board (PCB), without a wireless module and without a battery. In this configuration the control device is formed to be entirely passive in operation, thus eliminating the issues with regard to control devices connected to medical devices and systems using wired connections and wireless transmission modules.

10 Claims, 3 Drawing Sheets

(51) Int. Cl.
*G05B 19/414* (2006.01)
*A61B 17/00* (2006.01)
*A61B 90/98* (2016.01)
*A61B 6/00* (2006.01)

(52) U.S. Cl.
CPC ............... *A61B 6/467* (2013.01); *A61B 6/502* (2013.01); *A61B 6/504* (2013.01); *A61B 2017/00212* (2013.01); *A61B 2017/00221* (2013.01); *A61B 2017/00973* (2013.01); *G05B 2219/15117* (2013.01); *G05B 2219/23056* (2013.01)

(56) References Cited

U.S. PATENT DOCUMENTS

| | | | |
|---|---|---|---|
| 7,737,849 B2 | 6/2010 | Hwang et al. | |
| 8,159,370 B2 | 4/2012 | Shields et al. | |
| 8,274,610 B2 | 9/2012 | Clay, Jr. | |
| 8,380,126 B1* | 2/2013 | Ma | A61B 5/7475 455/41.2 |
| 8,961,441 B2* | 2/2015 | Cioanta | A61M 37/0092 601/2 |
| 9,658,178 B2* | 5/2017 | Surman | G01N 27/023 |
| 2003/0016136 A1* | 1/2003 | Harvey | H01H 9/167 340/686.1 |
| 2006/0210277 A1 | 9/2006 | Dubnack et al. | |
| 2007/0114621 A1* | 5/2007 | Wisnudel | G09F 3/0291 257/414 |
| 2007/0194100 A1* | 8/2007 | Plassky | G06K 19/0704 235/375 |
| 2008/0119843 A1* | 5/2008 | Morris | A61B 18/042 606/37 |
| 2008/0285626 A1* | 11/2008 | Claus | H04W 12/06 375/133 |
| 2008/0287062 A1* | 11/2008 | Claus | H04W 12/02 455/41.2 |
| 2009/0026392 A1* | 1/2009 | Yoshimi | A61B 6/4283 250/582 |
| 2010/0179542 A1* | 7/2010 | Joseph | A61B 18/1206 606/42 |
| 2010/0262139 A1 | 10/2010 | Beller et al. | |
| 2010/0283599 A1* | 11/2010 | Ma | A61B 34/74 340/539.1 |
| 2011/0189957 A1 | 8/2011 | Hocke | |
| 2015/0220763 A1* | 8/2015 | Porzelt | G08C 17/00 340/10.1 |
| 2015/0250439 A1* | 9/2015 | Ishii | A61B 6/54 378/115 |
| 2015/0342677 A1* | 12/2015 | Chalfant | A61B 18/20 606/11 |
| 2018/0113983 A1* | 4/2018 | Sridharan | A61B 90/98 |
| 2018/0303694 A1* | 10/2018 | Steenstra Toussaint | A61G 15/10 |

FOREIGN PATENT DOCUMENTS

| | | | |
|---|---|---|---|
| EP | 3 041 011 A1 | 7/2016 | |
| EP | 3315080 A1 * | 5/2018 | ............. A61B 90/98 |

* cited by examiner

PASSIVE WIRELESS FOOTPEDAL FOR MEDICAL APPLICATIONS

BACKGROUND OF INVENTION

The invention relates generally to controls for medical devices and systems and more specifically to a foot pedal for use in controlling a medical device or system.

In medical procedures it is often necessary for a physician to operate a medical device or system in association with the medical procedure being performed by the physician. However, in many situations the hands of the physician are occupied in holding the implements being utilized to perform the procedure. As a result, it is necessary to provide the physician with controls for the medical device or system that can be operated without the physician having to use their hands.

One example of a control utilized for this purpose is a foot pedal. The pedal is operably connected to the medical device or system and can be depressed by the physician in order to activate one or more function of the device or system, without the physician having to release their hold on the implements being utilized in performance of the medical procedure.

In certain prior art solutions to this issue, the foot pedal is connected to the medical device or system via a direct wired connection. The wire or cable extending between the pedal and the device or system enables the activation of the foot pedal by the physician to be transmitted directly to the device for use in activation of the device. Further, the cable can be used as a power source for the foot pedal, enabling the pedal to be powered by the medical device r system to which it is attached by the cable. However, the use of a cable to connect the pedal to the device or system necessarily can cause issues with the cable being inadvertently disconnected or becoming damaged rendering the cable and footpedal inoperative.

Other alternative solutions include wirelessly connecting the footpedal to the medical device or system. To do so, any number of wireless modules employing a standard wireless protocol, such as infrared, Bluetooth®, or Zigbee®, among others can be positioned within the footpedal and operably connected to suitable electronics, all of which are powered by a power source or battery disposed within the footpedal. In this configuration any issues involving a cable are avoided with the footpedal also being able to be positioned at various locations with respect to the medical device or system to communicate wirelessly therewith. However, in the wireless configuration, issues are still present. More particularly, due to the increased range of operation provided by the use of wireless communication between the pedal and the medical device or system, the potential of inadvertent activation of the device or system by the pedal is increased. Also, with regard to the ability to power the wireless footpedal, the power source/battery must be charged and/or replaced periodically to ensure proper functioning of the foot pedal. The charging or replacement is a concern for the end user as the charging and/or replacement must be done by the end user of the foot pedal and the end user must be check the status of the battery to determine if it require replacement. There is also the potential for a short or leakage from the battery and the battery must be properly disposed of once replaced by the end user. All of these issues with the battery contribute to significant increases in the service costs from the use of a wireless connection configuration for the footpedal.

Accordingly, it is desirable to develop a footpedal for use in conjunction with a medical device or system that can effectively communicate with the medical device or system but without the deficiencies of the prior art footpedal configurations.

BRIEF DESCRIPTION OF THE INVENTION

There is a need or desire for a control device for use in connection with a medical device or system in order to operate various functions of the medical device or system that does not require a wired connection or internal power source for the operation of the control device. The control device in certain embodiments can take the form of a footpedal that is formed without electronics, without a printed circuit board (PCB), without a wireless module and without a battery. In this configuration the control device is formed to be entirely passive in operation, thus eliminating the issues with regard to control devices connected to medical devices and systems using wired connections and wireless transmission modules.

According to one exemplary non-limiting aspect of the invention, the control device can take the form of a footpedal including a lower portion adapted to rest on a surface and an upper portion pivotally secured to the lower portion in order to be movable with respect to the lower portion. The footpedal includes a radio frequency identification (RFID) device or tag disposed on the upper or lower portion of the footpedal. The RFID tag is passive in that it is operated in response to an electromagnetic field received by the tag from a reader antenna disposed on the medical device or system with which the footpedal is utilized. The RFID tag is disposed on the footpedal adjacent a metal sheet or coating that functions as a shield for the RFID tag to prevent the electromagnetic field from the reader antenna from reaching the tag when the footpedal is in the inactivated position. However, when the upper portion of the footpedal is moved by a user, such as by applying pressure to the upper portion of the footpedal, the metal shield is displaced from the RFID tag, enabling the electromagnetic field to be received by the RFID tag. This powers the passive RFID tag and enables the tag to send a signal that is received by the reader antenna. Consequently, when the signal from the tag is received by the antenna, the antenna can direct the signal to the medical device or system which can initiate a function or action of the medical device or system associated with the signal from the RFID tag. To cease the operation of the function, the user can remove the pressure from the footpedal, thereby allowing the metal shield to be repositioned in the shielding location immediately adjacent the RFID tag. Further, as the RFID communication range is limited to few meters, the use of RFID tags nullifies the risk of inadvertent operation of the system function posed by other wireless communication having increased communication ranges.

According to one exemplary non-limiting embodiment of the invention, a control device for operating a function of a medical device or system includes a lower portion, an upper portion movably connected to the lower portion and an identification device adapted to communicate wirelessly with the medical device or system disposed on one of the lower or upper portion, wherein the control device does not include a power source.

According to another exemplary non-limiting embodiment of the invention, a medical system includes an imaging system, an identification device reader operably connected to the imaging system and a control device including an identification device operably connectable to the identification device reader to operate a function of the imaging system, wherein the control device is entirely passive.

According to still a further aspect of one exemplary non-limiting embodiment of the invention, a method of controlling the operation of a function of a medical system during a medical procedure includes the steps of providing medical system comprising an imaging system, an identification device reader operably connected to the imaging system and a control device including an identification device operably connectable to the identification device reader to operate a function of the imaging system, wherein the control device is entirely passive, unshielding the identification device to a signal from the identification device reader, receiving at the reader an operational control signal from the identification device and controlling operation of a function of the medical system in response to the control signal.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The drawings illustrate the best mode presently contemplated of carrying out the disclosure. In the drawings.

DETAILED DESCRIPTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
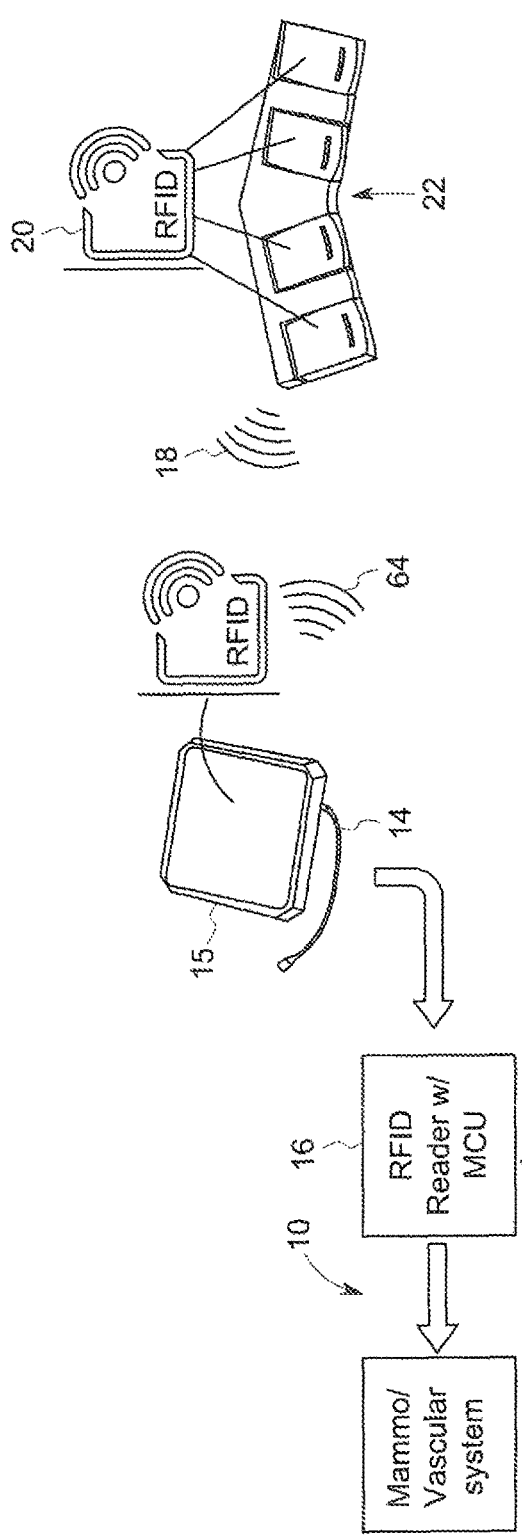
FIG. 1 is a schematic representation of an medical imaging device and/or system including a control device according to one exemplary non-limiting embodiment of the invention.

Referring to FIG. 1, in the illustrated exemplary non-limiting embodiment a medical imaging system 10, such as a mammography or vascular imaging system, is operably connected to a radio frequency identification (RFID) reader 12. The reader 12 is also operably connected via a cable 14 or other suitable connector to an antenna 15 operably connected the reader 12 to the system 10. The reader 12 additionally includes a microprocessor control unit (MCU) 16 that is configured to receive operational control signals 18 from an associated RIFD tag 20 in response to querying/powering signals 64 emitted by the antenna 15 which is powered by the system 10 or can be independently powered. The MCU 16 can interpret the signals 18 received from the tags 20 via the reader 12 and can determine a function of the system 10 that is to be activated by in response to the signals 18. This information is relayed from the MCU 16 to the system 10 in order to operate the function of the system 10 as desired.

Referring now to FIGS. 1-4, in the illustrated exemplary and non-limiting embodiment, the RFID tag 20 is disposed on a control device 22. The control device 22 can take a variety of forms and in the illustrated embodiment is formed as a footpedal 24. The footpedal 24 includes a lower portion 26 formed of a rigid material, such as a plastic or non-metal, non-conductive material, and having a bottom surface 28, a pair of opposed end walls 30 extending upwardly therefrom and a pair of sidewalls 32 extending upwardly from the bottom surface 28 between and connected to the end walls 30. The side walls 32 each includes a pivot aperture 34 formed therein at a midpoint 36 of the side walls 32. Further, each of the side walls 32 is formed with sloped sections 37 extending downwardly from the midpoint 36 to each end wall 30, placing the midpoint 36 at the highest point of the side wall 32.

Figure 2:
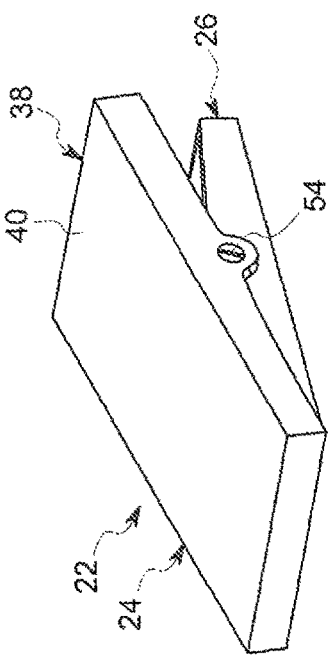
FIG. 2 is an isometric view of a control device according to an exemplary non-limiting embodiment of the invention in a non-use configuration.

The footpedal 24 also includes an upper portion 38 formed of a rigid material, such as a plastic or non-metal, non-conductive material, similarly to the lower portion 26 and including an upper surface 40, a pair of end walls 42 extending downwardly from the upper surface 40 and a pair of side walls 44 extending downwardly from and connected between the end walls 42. The side walls 44 further include pivot openings 46 located at the midpoints 48 of the side walls 44. The perimeter 50 of the upper portion 38 is slightly larger than the perimeter 52 of the lower portion 26 such that the end walls 42 and side walls 44 of the upper portion 38 can be positioned outside of the corresponding end walls 32 and side walls 34 of the lower portion 26. In this position, the pivot apertures 34 are aligned with the pivot openings 46 and can receive a pivot pin 54 therethrough to secure the upper portion 38 to the lower portion 26. Further, when secured to one another, the sloped sections 37 of the side walls 34 allows the upper portion 38 to be moved about the pivot pin 54 between angled positions on either side of the midpoint 36, as shown in FIGS. 2 and 3.

Figure 3:
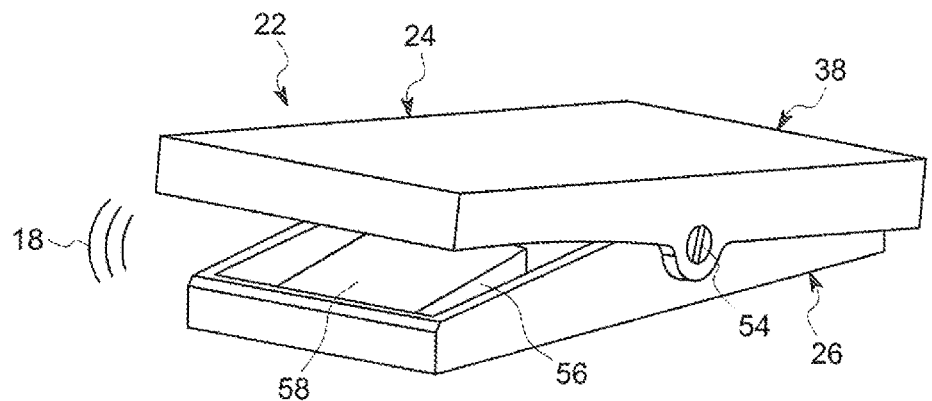
FIG. 3 is an isometric view of the control device of FIG. 2 in a use configuration.
Figure 4:
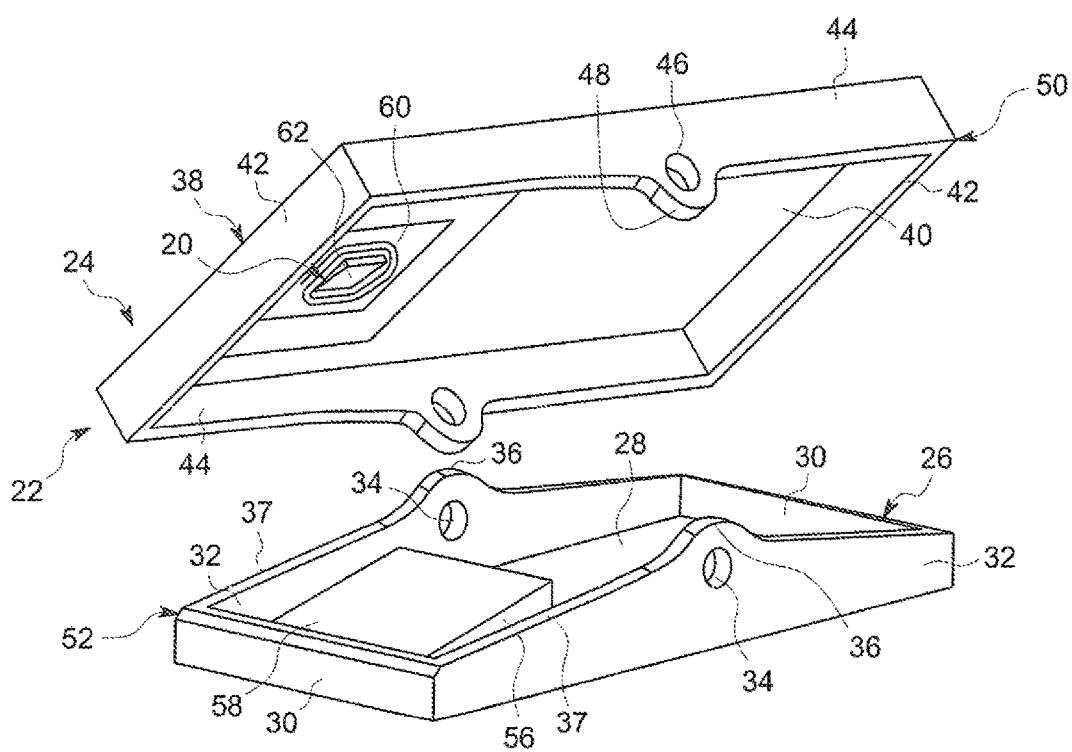
FIG. 4 is an isometric exploded view of the control device of FIG. 2.

Looking now at FIGS. 3 and 4, the lower portion 26 of the footpedal 22 additionally includes a pedestal 56 disposed on the bottom surface 28 between the side walls 32 and adjacent one end wall 30, such that the pedestal 56 is located to one side of the midpoint 36. The pedestal 56 supports a metal sheet or coating 58 thereon.

On the upper portion 38, the RFID tag 20 is disposed on the upper surface 40 between the side walls 44 and adjacent one end wall 42, so as to position the tag 20 in alignment with the metal sheet 58 located on the pedestal 56. The RFID tag 20 is a passive RFID tag 20, such that the tag 20 does not include any electronics, a printed circuit board (PCB), a wireless module or a battery. The passive RFID tag 20 is formed with a radio frequency (RF) antenna 60 with a small, unpowered chip 62 connected thereto that is operable within a specific range of frequencies of signals that are received by the antenna 60. When an querying/powering signal 64 within that frequency range sent from the antenna 15 is received by the antenna 60, the antenna 60 creates a magnetic field from which the chip 62 can derive power in order to send the information about the tag 20 and function of the imaging system 10 to be operated encoded on the chip 62 via a return operational control signal 18.

In operation of the control device 22, the footpedal 24 is initially placed within an area around the medical device or system 10 within easy reach of the physician performing the procedure. The footpedal 24 is initially configured such that the upper portion 38 is pivoted to position the RFID tag 20 immediately adjacent and/or in contact with the metal sheet 58 disposed, on the pedestal 56 of the lower portion 26. The metal sheet 58 and the parts of the lower portion 26 and upper portion 38 to which the tag 20 is secured act a shield/shielding member for the tag 20 according to the Faraday cage principle, preventing the signal emanating from the reader 12 from reaching the tag 20. The upper portion 38 can be biased to remain in the configuration where the tag 20 is shielded by the metal sheet 58, such as by weighting the upper portion 38 or providing a suitable biasing member (not shown) between the upper portion 38 and the lower portion 26. In this configuration, the querying/powering signals emanating from the antenna 15 are not received by the tag 20, as the tag 20 is shielded by the shielding enclosure provided or formed by the upper portion 38, the lower portion 26 and/or the metal sheet 58, and no corresponding signal 18 from the tag 20 is received by the reader 12 in order to operate the selected function of the system 10.

When the physician desires to active the function of the system 10 controlled by the control device 22, the physician can depress or pivot the upper portion 38 relative to the lower portion 26 to move the tag 20 away from the metal sheet 58, exposing or unshielding the tag 20 to the querying/powering signal 64 from the antenna 15 The signal 64 is received by the passive tag 20 and powers and causes the chip 62 thereon to send the corresponding operational signal 18 to the reader 12. The operational signal 18 received by the reader 12 is utilized by the MCU 16 to operate the associated function of the system 10 as desired by the physician. Depending upon, the particular function of the system 10 being controlled, the physician can operate the control device 22 by depressing and releasing the upper portion 38 of the footpedal 24, by depressing and holding the upper portion 38 in the depressed position, or by depressing the upper portion 38 in a predetermined pattern to provide a desired activation or operation pattern of the function of the system 10 being controlled.

In additional non-limiting exemplary embodiments, the control device 22 can utilize other methods for shielding the tags 20, such as by unrolling the tags 20 from a metal enclosing roll upon actuation of the control device 22, or by moving the tags 22 out of a metal enclosure (not shown) upon actuation of the control device 22, such as by depressing the upper portion 38 of the footpedal 24.

In addition to directly controlling the function of the system 10, the actuation of the control device 22 can be utilized in an alternative non-limiting exemplary embodiment as a switch for the medical device 10. For example, upon depressing the footpedal 24, the exposure of the tag 20 to the signal 64 from the reader 12 causes the tag 20 to emit the signal 18 to be received by the reader 12. This signal 18 can be utilized by the reader 12 to indicate to the system 10 the status of a switch (not shown) for the system 10, such as whether the switch is to be considered activated. Thus, the control device 22 can be utilized as a remote activation of a switch on the system 10 for a function of the system 10, whether or not the system 10 has an actual switch for the particular function. In addition by having two switches (not shown) associated with the control device 22, redundancy can be achieved. This is accomplished as the status of both the switches would be sent along with the tag id signal 18 which would be sensed by the reader 12. Thus, only when both the switches are activated and the signal 18 is received by the reader 12 would the system 10 activate the function. In an alternative embodiment, the status of two separate switches/control device 22 are embedded with tag data 18 on tags 20 associated with each switch/control device 22. For the reader 12 to read the switch status, tag 20 should be exposed and read. This embodiment is applicable to both systems 10 with and without metal shielding 58. If there is no metal shielding 58 on the switch 22, the tag 20 will be continually exposed but the system 10 will not perform the required operation until unless both the switches 22 are pressed, i.e., both tags 20 are simultaneously exposed or covered. In this embodiment the main concern is the use of the two switches 22 to avoid single fault condition that can be causes where single switch/control device 22 is utilized.

Figure 5:
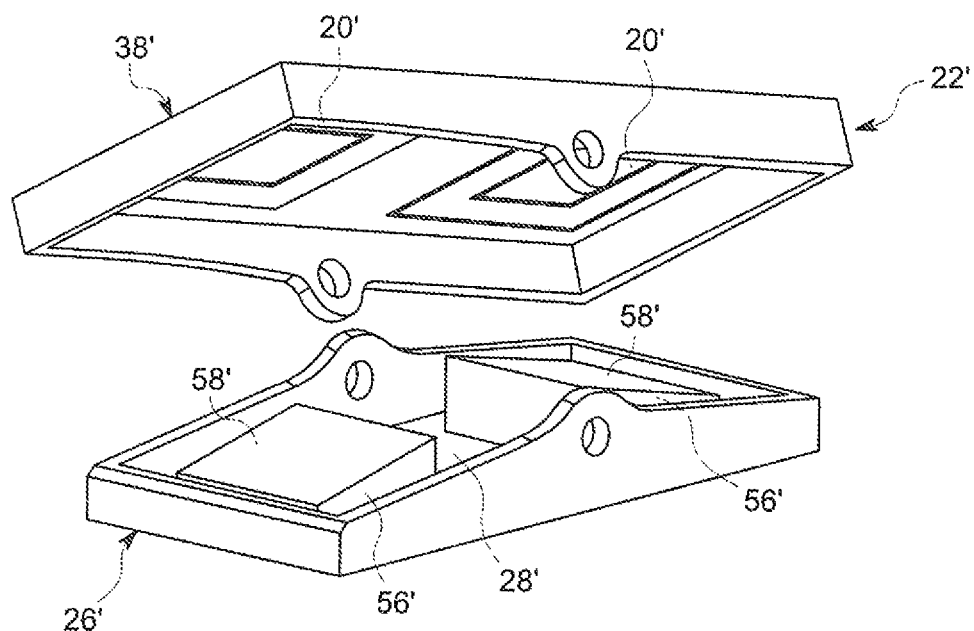
FIG. 5 is an isometric exploded view of a control module according to another exemplary non-limiting embodiment of the invention.

Looking now at FIG. 5 in another illustrated non-limiting exemplary embodiment, the control device 22' is illustrated in which the upper portion 38' includes a pair of tags 20' located on the upper surface 40' with a corresponding pair of pedestals 56' and metal sheets 58' located on the bottom surface 28' of lower portion 26'. In this control device 22', one tag 20' is always in an exposed position such that the reader 12 will receive a signal 18 from one of the tags 20' regardless of the position of the upper portion 38'. One tag 20' is identified with the operation of the selected function of the system 10, while the other tag 20' is identified with the non-operation of the selected system function. Thus, when the upper portion 38 of the pedal 24 is depressed/operated to expose the tag 20' corresponding to the operation of the function, the tag 20' corresponding to the non-operation of that function is simultaneously shielded. In this manner, the control device 22 provides redundancy in the operation of the device 22' to avoid unwanted activation of the system function in the situation where neither or both of the tags 20' emit signals that are received by the reader 12, such as in the following Table showing the operational conditions illustrated by the sensing of the tags 20', where a 1 indicates the tag 20' is sensed by the reader 12 and a 0 indicated the tag 20' is not sensed by the reader 12:

TABLE 1

Output Configurations of Multiple Tag Control Device

| Tag 1 | Tag 2 | Output to System | Condition |
|---|---|---|---|
| 0 | 0 | 0 (both tags not sensed) | Fault |
| 0 | 1 | 0 | Normal (unactuated) |
| 1 | 0 | 1 | Pedal Actuated |
| 1 | 1 | 0 (both tags sensed) | Fault |

Figure 6:
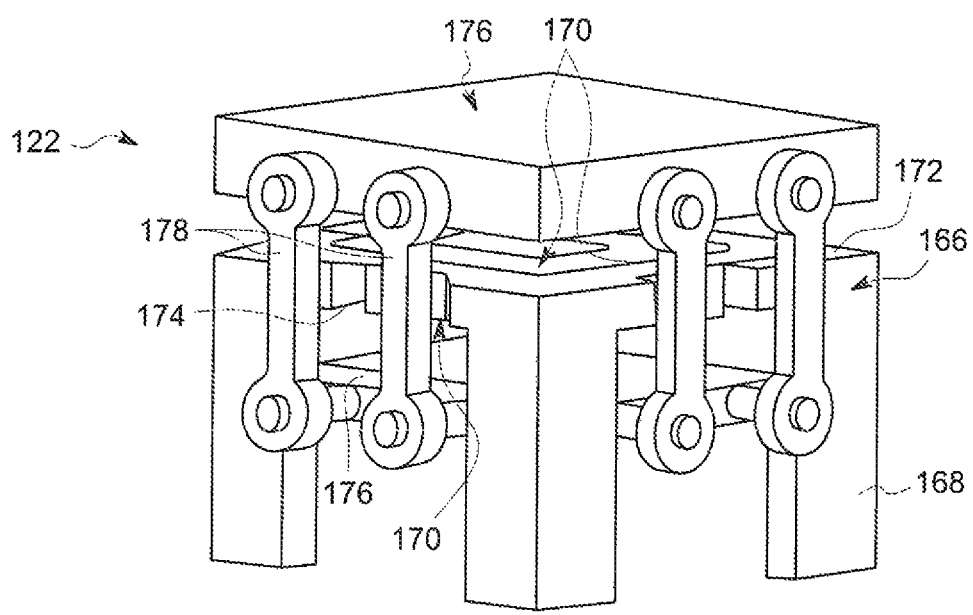
FIG. 6 is an isometric view of a control module according to still another exemplary non-limiting embodiment of the invention.

Referring now to FIG. 6 in another illustrated non-limiting exemplary embodiment the control device 122 can include a central platform 166 mounted to a number of supports 168. A tag 170 is disposed on an upper surface 172 and a lower surface 174 of the platform 166. Shielding members 177 are disposed adjacent the upper surface 172 and the lower surface 174 on movable panels 176 that are interconnected with one another by braces 178 that are disposed between and outside of the perimeter of the supports 168. The braces 178 enable the panels 176 supporting the shielding members 177 to move in conjunction with one another against the bias of a biasing member (not shown) engaged between the panels 176 and the platform 166 to bias the shielding members 177 toward the lower surface 174, thus exposing the tag 170 located on the upper surface 172, which can be the tag 170 associated with the non-operation of the system function. Thus, when a user applies a force against the upper panel 176 against the bias of the biasing member, the panel 176 and corresponding lower shielding member 177 is displaced from the lower surface 174, exposing the tag 170 thereon, while the upper panel 176 and corresponding shielding member 177 simultaneously covers and shields the tag 170 on the upper surface 172. In this manner, the tag 170 on the lower surface 174 is exposed and transmits the signal 18 corresponding to the operation of the associated system function. In an alternative and non-limiting exemplary embodiment, the positions of the tags 170 and the shielding members 177 can be reversed, with the shielding members 177 being disposed on the upper surface 172 and lower surface 174 of the platform 166 and the tags 170 located adjacent the upper surface 172 and/or lower surface 174 on the movable panels 176.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A control device for operating a function of a medical device or system, the control device comprising:
    a lower portion;
    an upper portion movably connected to the lower portion;
    an identification device adapted to communicate wirelessly with the medical device or system disposed on one of the lower or upper portion; and
    at least one shielding member disposed on one of the lower portion or the upper portion,
wherein the control device does not include a power source.

2. The control device of claim 1 wherein the control device does not include an electronic component or wireless transmission module.

3. The control device of claim 1 wherein the identification device is a passive identification device.

4. The control device of claim 3 wherein the passive identification device is a passive RFID tag.

5. The control device of claim 1 wherein the at least one shielding member is the upper portion.

6. The control device of claim 1 wherein the at least one shielding member is a metal sheet disposed on the lower portion.

7. The control device of claim 1 wherein the metal sheet is disposed on a pedestal located on the lower portion in selective alignment with the identification device.

8. The control device of claim 1 further comprising a number of identification devices disposed on one of the upper portion or lower portion.

9. A control device for operating a function of a medical device or system, the control device comprising:
    a lower portion;
    an upper portion movably connected to the lower portion; and
    an identification device adapted to communicate wirelessly with the medical device or system disposed on one of the lower or upper portion, wherein the control device does not include a power source, and wherein the upper portion is pivotally connected to the lower portion to selectively expose the lower portion.

10. The control device of claim 1 wherein the shielding member is selectively positionable over the identification device.

* * * * *